United States Patent [19]

McDaniel

[11] Patent Number: 5,209,718
[45] Date of Patent: May 11, 1993

[54] PRESSURE APPLYING BANDAGE OR DRSSSING FOR SUPERFICIAL WOUNDS

[76] Inventor: William R. McDaniel, 9158 Saddle Bow Dr., Brentwood, Tenn. 37027

[21] Appl. No.: 783,230

[22] Filed: Oct. 28, 1991

[51] Int. Cl.$^5$ ............... A61F 13/00; A61F 15/00; A61F 5/28; A61F 5/30
[52] U.S. Cl. .................... 602/53; 602/41; 128/888; 128/109.1; 128/111.1; 128/117.1
[58] Field of Search ............ 128/155, 156, 89 R, 128/90, 106.1, 108.1, 109.1, 111.1, 117.1, 121.1, 125.1, 126.1, 767, 157, 158, 160, 168, 169, 171, 888; 602/3, 6, 20–22, 30–31, 41, 53, 58

[56] References Cited

U.S. PATENT DOCUMENTS

| | | | |
|---|---|---|---|
| 551,237 | 12/1895 | Stewart | 128/106.1 |
| 2,226,546 | 12/1940 | Bower | 128/156 |
| 3,155,096 | 11/1964 | Outwin | 128/171 |
| 4,053,053 | 10/1977 | Tumangday | 128/156 |
| 4,991,573 | 2/1991 | Miller | 128/106.1 |

Primary Examiner—Randall L. Green
Assistant Examiner—Paul Zuttarelli

[57] ABSTRACT

A disposable pressure applying bandage for superficial wounds comprises a pad, for placement on a wound, a flexible arcuate member having its convex surface against the pad, and adhesive material extending over the arcuate member, for attachement of the arcuate member and the pad over the wound. Attachment of the adhesive material to a patient's skin flattens the arcuate member, to a lesser or greater degree, applying pressure to the wound.

6 Claims, 1 Drawing Sheet

PRESSURE APPLYING BANDAGE OR DRSSSING FOR SUPERFICIAL WOUNDS

This invention relates to pressure applying bandages or dressings for superficial wounds, and in particular to self adhesive disposable bandages. The invention also relates to the applying of pressure to a wound.

Disposable bandages, particularly of the self adhesive type, are used widely to cover and protect superficial wounds. In many cases the conventional form of such bandages is adequate. However, in some instances, flow of blood or other fluids from wounds, such as cuts and abrasions, is more serious than can be stopped by these bandages.

The general form of disposable bandage generally comprises a pad for positioning on and over the wound, being generally sterile and non-sticking. This is backed by a piece of pressure adhesive material which holds the pad on the wound. The shape can vary, being square, elongate, circular and other. In some circumstances a separate pad is placed over the wound and then a piece of pressure adhesive material placed over the pad and into contact with the patient's skin to hold the pad in place.

Limited pressure can be applied with the conventional bandage or dressing. Some pressure can be applied when the wound is on a rounded part of a body, such as a finger, arm, or other well rounded part. On a flat or only slightly rounded part of the body, such as back, chest, top part of legs and similar parts, minimal or no pressure can be applied to the wound.

Various attempts have been made to provide pressure. In U.S. Pat. Nos. 4,005,709, 4,377,159 and 4,971,046, pads are provided for localizing pressure. The bandage in 4,005,709 is not of the self adhesive type, the bandage being wound round an area or similar, over the pad. In U.S. Pat. No. 4,377,159, an adhesive tape has a section of resilient foam which is held partially compressed by the tape. Such a pad is bulky and can make it awkward to wear such a dressing. A non-stick sterile layer must be provided over the pad to prevent adhering to wound. In U.S. Pat. No. 4,971,046, similarly, an adhesive tape holds down a section of resilient foam. U.S. Pat. No. 4,243,028 provides a strap for wrapping round a limb, with a pad of resilient members held against the limb. This cannot be used as a localized dressing. U.S. Pat. No. 4,224,945 has an inelastic strut for positioning over a wound, with an expansible pouch. The pouch is inflatable, as by a pump. Alternatively the pouch can contain a powder and a frangible capsule containing liquid, the liquid when released reacting with the powder to form a gas for inflating the pouch. This is a complex and relatively expensive bandage.

The present invention provides a bandage or dressing which can be applied to a wound and which will apply a pressure to the wound.

Particularly, the invention provides a disposable bandage or dressing having a pad for positioning over and on the wound, a flexibly resilient arcuate member for positioning over the pad, the arcuate member having a convex surface facing towards the pad, and an adhesive layer over the plastic member and extending beyond the plastic member and the pad for attachment to the body of a patient.

In the broadest concept, a dressing can comprise separate pads and an arcuate plastic member, the two, when in position, then held in place by adhesive material.

Conveniently a bandage will comprise pad, plastic member and adhesive material pre assembled together, with a removable covering over the pad.

The invention will be readily understood by the following description of certain embodiments, by way of example, in conjunction with the accompanying drawings, in which:

FIGS. 1, 2 and 3 illustrate an embodiment of the invention in which the various items are pre assembled into a dressing, such as are provided in boxes and packages for emergency home, hospital and other needed usage.

Figure 1:
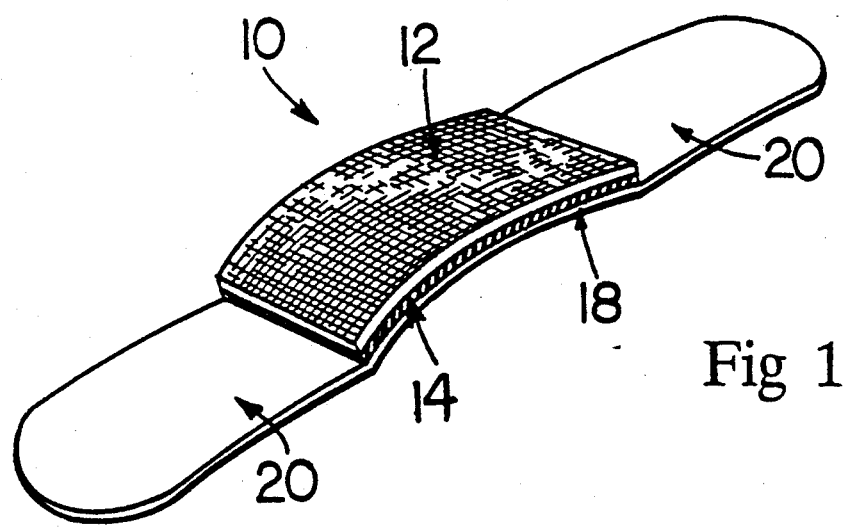
FIG. 1 is a perspective view of one form of bandage in accordance with the invention.
Figure 2:
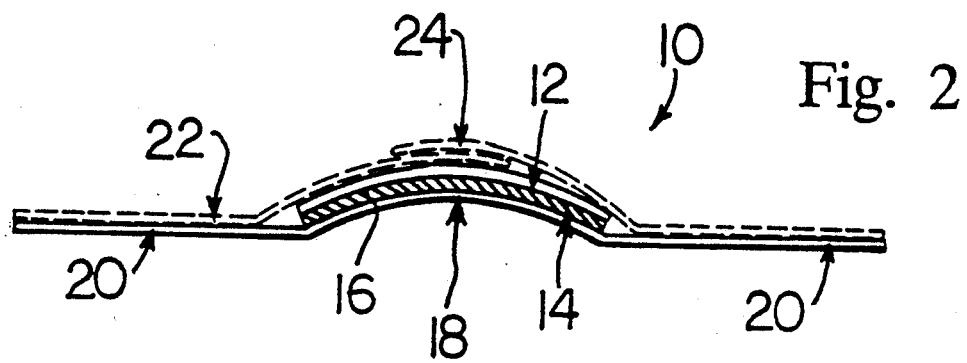
FIG. 2 is a side view of the bandage in FIG. 1 in the pre applied form.

As illustrated in FIGS. 1 and 2, a disposable pressure applying bandage 10 comprises a pad 12, generally sterile and of non-stick material, for example gauze folded to form the pad. On the rear surface of the pad is a thin arcuate member, in the form of a strip of flexible material, 14, for example of plastic. The strip 14 has its convex surface 16 positioned against the pad 12. Backing the plastic strip 14 is a strip of self adhesive material 18. The adhesive material extends beyond the strip 14, in opposite directions, forming attachment members 20. Normally such a bandage will be supplied with a covering member comprising two overlapping strips of material 22 and 24, shown in dotted outline in FIG. 2. The strips 22 and 24 are adhered to the attachment members 20 and also adhere to each other for part of the overlap, an end of the outer strip, for example 24, being free for removal.

Figure 3:
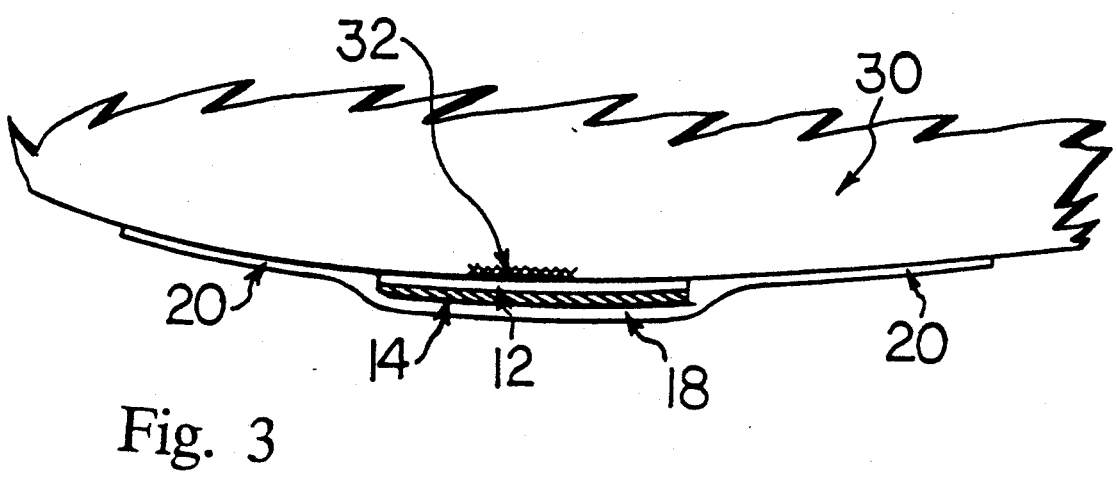
FIG. 3 is a side view of the bandage in FIG. 1 applied to a body part.

FIG. 3 illustrates a bandage of the form as in FIGS. 1 and 2, applied to a part of the body 30. A wound area is indicated at 32. To apply, the covering member strips 22 and 24 are removed and the pad 12 positioned over the wound. The two attachment members 20 are then pulled apart and pushed down to adhere to the skin of the body part. In so doing the arcuate strip 14 is straightened to a greater or lesser extent, depending on how firmly the members 20 are pulled outwards as they are also applied to the skin. On release of pressure on the covering member 18 and members 20, the strip 12 attempts to regain its original shape. This results in pressure being applied, through the pad, to the wound area.

The pressure applied can be varied, by a variety of means. For example, the thickness of the strip 14 can be varied to provide a means for increasing or decreasing the pressure which will be applied. Also the curve of the strip can be varied and also the stiffness, to give the same ability to vary the pressure applied. Heat forming the plastic strip into configurations to fit hard-to-cover body parts, such as ears or nose, could greatly simplify applying good tight dressings to these areas. Dressings having the same pressure characteristics can be boxed separately, or a box can contain a variety of dressings having different pressure characteristics. Preferably the pressure is below the venous pressure, for example between 8 and 40 mm of mercury.

The strip 14 can be of other material than plastic, for example metal. The strip 14 and pad 12, can be positioned on adhesive material which extends all round the pad and strip. The adhesive material would be elastic and the parts extending from the ends of the strip applied first. While the term strip has been used for convenience, and as the form usually provided, the arcuate member can vary in shape.

While it is convenient to provide the bandages in a pre assembled form, for supplying in packages, etc., a bandage can be formed from separate members at the time of use. Thus a pad can be positioned over a wound, and an arcuate member placed on the pad. A length of adhesive material is then applied to straighten the strip and hold it and the pad in position. In a pre assembled form, individual bandages could be enclosed in a sealed containing member.

A bandage or dressing, in accordance with the invention has a major advantage over other means, for example tourniquets, in that it is safer. The pressure applied would be insufficient to restrict blood-flow through major vessels like arteries and large veins, so that the risk of tissue damage due to lack of blood flow and oxygen would be minimal.

The invention can be used by individual consumers who often have need for better control of bleeding with household or industrial injuries prior to or in lieu of further medical attention. The invention can also be used by physicians and surgeons over minor surgery wounds, biopsy sites or following vein sclerotherapy, and when blood samples have been taken and similar actions, where compression enhances healing and lessens side effects. It can be used by emergency medical technicians to compress minor wounds at accidents while more major problems are attended. The invention can also be used to apply pressure at positions other than at wounds.

What is claimed is:

1. A pressure applying bandage for self adhesion to a skin surface of a patient, comprising:

a flexible pad for positioning on the skin surface;

a flexible resilient arcuate member having a periphery and opposed convex and concave surfaces, the convex surface in contact with said flexible pad;

a length of pressure adhesive material extending over said arcuate member and beyond the periphery of said arcuate member, and in adhesive contact with the concave surface;

said pressure adhesive material extending beyond the periphery of said member forming attachment means for adhesion to said skin surface at said periphery of said arcuate member to attach and flex said arcuate member to apply pressure to said pad.

2. A bandage as claimed in claim 1, including a removable cover member extending over said pressure adhesive material and said pad, removal of said cover member exposing said pressure adhesive material for adhesion to said skin.

3. A bandage as claimed in claim 2, wherein said cover member comprises two portions overlapping at a central position over said pad.

4. A bandage as claimed in claim 2, including a containing member, said pad, arcuate member and said adhesive means sealed within said containing member.

5. A bandage as claimed in claim 1, wherein said flexible arcuate member has a thickness adjusted to provide a desired pressure.

6. A dressing for a wound comprising:

a flexible pad, an arcuate flexible resilient member having a periphery and a length of pressure adhesive material in superimposed arrangement; a convex surface or said flexible resilient member in contact with said flexible pad and said pressure adhesive material extending over and in adhesive contact with a concave surface of said flexible resilient member, said pressure adhesive material extending beyond the periphery of said flexible resilient member and having segments which are pulled down on either side of said flexible resilient member adjacent said periphery for adhesion to a skin surface of said periphery to flex said resilient member and apply pressure through said pad on said skin surface.

* * * * *